(12) United States Patent
Dobashi

(10) Patent No.: US 8,770,756 B2
(45) Date of Patent: Jul. 8, 2014

(54) OPHTHALMIC APPARATUS

(75) Inventor: Yasuhiro Dobashi, Matsudo (JP)

(73) Assignee: Canon Kabushiki Kaisha, Tokyo (JP)

( * ) Notice: Subject to any disclaimer, the term of this patent is extended or adjusted under 35 U.S.C. 154(b) by 190 days.

(21) Appl. No.: 13/398,069

(22) Filed: Feb. 16, 2012

(65) Prior Publication Data

US 2012/0218521 A1  Aug. 30, 2012

(30) Foreign Application Priority Data

Feb. 28, 2011  (JP) ................................. 2011-042658

(51) Int. Cl.
*A61B 3/14* (2006.01)
*A61B 3/00* (2006.01)

(52) U.S. Cl.
USPC .......................................... 351/208; 351/245

(58) Field of Classification Search
USPC ................................................. 351/208, 245
See application file for complete search history.

(56) References Cited

U.S. PATENT DOCUMENTS

| | | | | |
|---|---|---|---|---|
| 4,743,107 | A * | 5/1988 | Aizu et al. ..................... | 351/221 |
| 5,905,562 | A * | 5/1999 | Isogai et al. .................. | 351/208 |
| 7,662,092 | B2 | 2/2010 | Miyagi et al. | |
| 2004/0267093 | A1 | 12/2004 | Miyagi et al. | |
| 2006/0262271 | A1* | 11/2006 | Schiabel et al. .............. | 351/212 |
| 2007/0171372 | A1* | 7/2007 | Seal et al. ..................... | 351/245 |
| 2009/0079939 | A1* | 3/2009 | Mimura ......................... | 351/245 |

FOREIGN PATENT DOCUMENTS

| | | |
|---|---|---|
| JP | 08-126611 A | 5/1996 |
| JP | 3276682 B2 | 4/2002 |
| JP | 2002-369799 A | 12/2002 |
| JP | 2003-230535 A | 8/2003 |
| JP | 2004-275504 A | 10/2004 |
| JP | 3672447 B2 | 7/2005 |
| JP | 2006-130227 A | 5/2006 |
| JP | 2008-061715 A | 3/2008 |
| JP | 4250062 B2 | 4/2009 |
| JP | 4265842 B2 | 5/2009 |
| JP | 4323209 B2 | 9/2009 |
| JP | 2009-268682 A | 11/2009 |

OTHER PUBLICATIONS

U.S. Appl. No. 13/398,031, filed Feb. 16, 2012, Akiba.
U.S. Appl. No. 13/398,053, filed Feb. 16, 2012, Inoue.

* cited by examiner

*Primary Examiner* — Jordan Schwartz
(74) *Attorney, Agent, or Firm* — Fitzpatrick, Cella, Harper & Scinto

(57) ABSTRACT

An ophthalmic apparatus in which a tilt angle of an operating rod corresponds to a position of an inspection unit adapted to inspect an eye to be examined, and a movable range of the inspection unit is wider than a tilt able range of the operating rod, the apparatus comprising: a detection unit adapted to detect the tilt angle of the operating rod by detecting an electrical signal generated by tilting the operating rod; a calculation unit adapted to calculate a position of the inspection unit which corresponds to the tilt angle; a moving unit adapted to move the inspection unit to a position calculated by the calculation unit; and a switching unit adapted to switch between interruption and resumption of calculation processing performed by the calculation unit.

4 Claims, 9 Drawing Sheets

F I G. 3
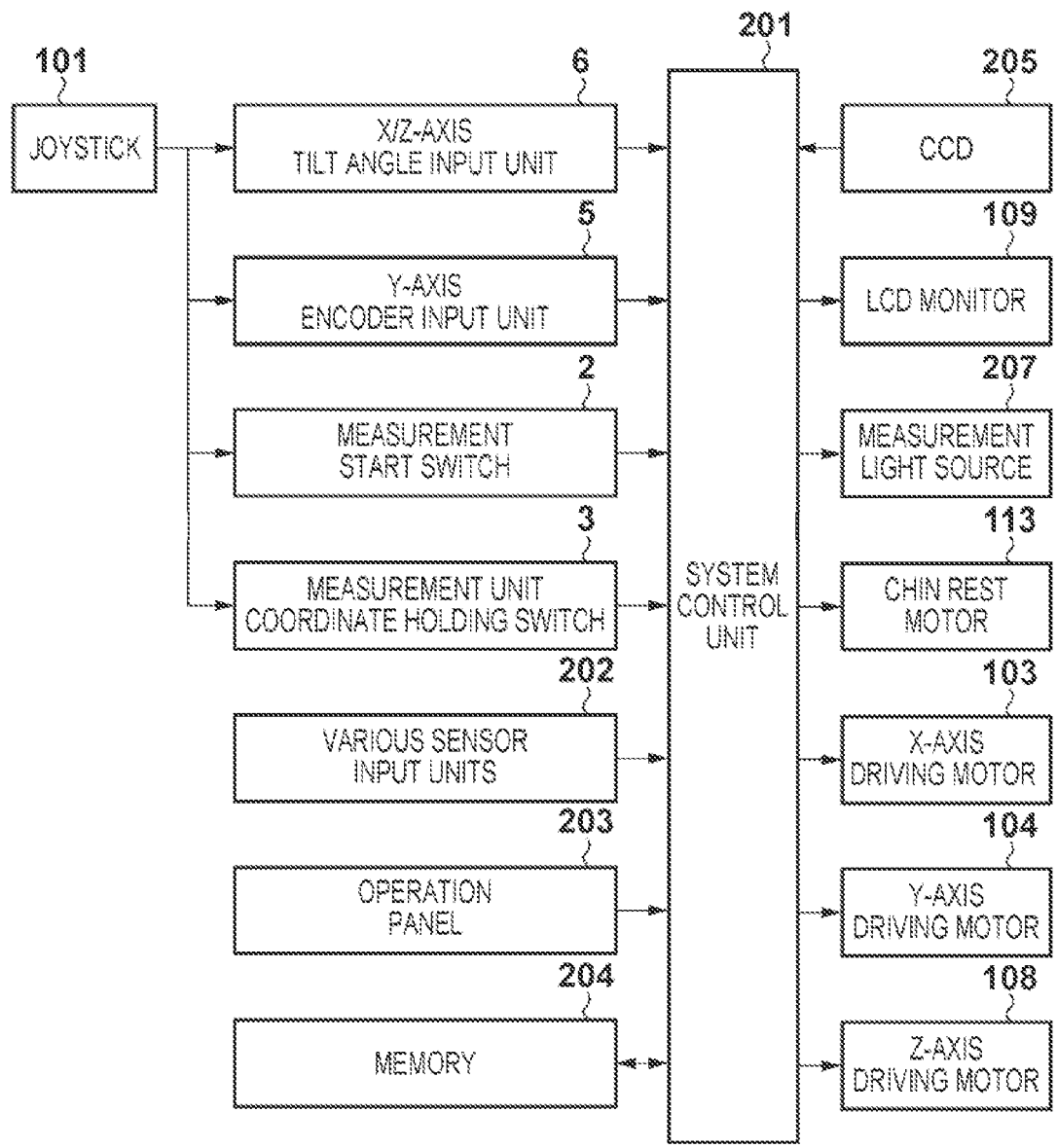

OPHTHALMIC APPARATUS

BACKGROUND OF THE INVENTION

1. Field of the Invention

The present invention relates to an ophthalmic apparatus and, more particularly, to an ophthalmic apparatus which aligns an eye to be examined with an inspection unit using a joystick to inspect, observe, and capture the eye.

2. Description of the Related Art

Many ophthalmic apparatuses include a base unit having a face rest that fixes the face of an object, an inspection unit which observes/captures and measures the eye to be examined, a stage unit which moves the inspection unit in the backward/forward, leftward/rightward, and upward/downward directions relative to the base unit, and a joystick mechanism which is operated to drive the stage unit.

Many conventional ophthalmic apparatuses use a manual stage which mechanically links a joystick mechanism to a stage unit, and mechanically drive an inspection unit by using the joystick mechanism (to be referred to as the manual joystick hereinafter). Recently, there are an increasing number of ophthalmic apparatuses which include an electric stage driven by a motor or the like owing to advantages such as automatic alignment. Unlike a conventional joystick mechanism, the electric stage cannot be moved by using a mechanical link. For this reason, such an apparatus includes an electric joystick capable of performing control using electric signals as a drive instruction input device for an electric stage unit.

As a manual joystick mechanism, there is known a mechanism based on a scheme in which an examiner moves an inspection unit by tilting the operating rod on the contact point, as an operation supporting point, between a hemispherical support member disposed under the operating rod and a friction plate disposed on the apparatus base portion side. When wanting to largely move the inspection unit, the examiner increases the angle at which the operating rod tilts (to be referred to as a tilt angle hereinafter). When wanting to slightly move the inspection unit, the examiner decreases the tilt angle. The operating rod can tilt in all directions centered on a neutral point. It is possible to freely move the inspection unit based on the tilt angle and direction of the operating rod. In addition, the joystick used in the ophthalmic apparatus needs to have both the functions of performing fine motion operation required for alignment with the eye to be examined and coarse motion operation required for switching between the left and right eyes. When switching between the left and right eyes by using a joystick based on a scheme of manually driving the inspection unit, the examiner can easily switch between the left and right eyes by sliding the joystick on a friction plate. The examiner often performs this operation at the time of fine motion operation, and uses it to change the tilt angle of the joystick without moving the inspection unit. For example, this operation is used in the following case. After the left and right axes align with each other, the examiner raises the operating rod in a tilted state to the neutral state while sliding it with the inspection unit being fixed, and then performs alignment in the forward/backward direction.

On the other hand, there is known an electric joystick which electrically reads the tilt angle of the operating rod and drives the inspection unit based on the read information so as to obtain operational feeling similar to that obtained from the manual joystick scheme. A joystick based on this scheme is mechanically configured to make the inspection unit perform "fine motion" when being operated in a predetermined tilt angle range (for example, from −20° to +20°) and to make the inspection unit perform "coarse motion" when being operated beyond the predetermined tilt angle range (see Japanese Patent Laid-Open No. 2002-369799).

In addition, since the moving velocity of the inspection unit depends on the degree of skill in operation of the examiner, an electric joystick capable of changing the moving velocity of the inspection unit in the upward/downward direction is also known (see Japanese Patent Laid-Open No. 8-126611).

Joysticks are frequently used in the medical equipment field other than ophthalmic apparatuses. For example, a joystick is used to operate an endoscope. Joysticks capable of operating electric driving units are widely used in endoscopes to determine the bending directions of the distal ends of the camera units inserted into the human bodies. In the field of endoscopes, there have been disclosed many types of safety mechanisms for preventing the endoscope distal end portions inserted into the human bodies from damaging the bodies due to operation errors. As an example of a safety mechanism, there has been disclosed an intention detection unit which allows the examiner to input information which is provided, in addition to a joystick, for an endoscope (see Japanese Patent Laid-Open No. 2003-230535). According to Japanese Patent Laid-Open No. 2003-230535, a combination of an input from the intention detection unit and an input from the joystick is used to determine whether joystick operation is intended by the examiner or an operation error. The endoscope validates or invalidates the input instruction by joystick operation based on the determination result, and then controls the bending operation of the endoscope distal end portion.

The joystick disclosed in Japanese Patent Laid-Open No. 2002-369799 which operates the electric stage unit and the apparatus disclosed in Japanese Patent Laid-Open No. 8-126611 allows operation more similar to the operation of a conventional joystick mechanism based on the manual driving scheme.

The electric joystick disclosed in Japanese Patent Laid-Open No. 2002-369799, however, gives no consideration to the sliding operation of this manual joystick. For this reason, if the left and right axes align with each other when the operating rod has a given tilt angle, it is necessary to perform tilting operation back and forth while maintaining the tilt angle. This poses a problem that an alignment shift tends to occur in the leftward/rightward direction at the time of alignment in the forward/backward direction, resulting in difficulty in operation. When an integrated joystick is configured to implement coarse motion and fine motion, it is necessary to tilt the operating rod through a predetermined angle or more at the time of coarse motion. For this reason, when coarse motion has switched to fine motion, the operating rod has always tilted. It is difficult to raise the operating rod to the neutral state without moving the inspection unit from the position at which it has stopped at the time of coarse motion.

In addition, moving velocity settings are limited to those in the upward/downward direction in the apparatus disclosed in Japanese Patent Laid-Open No. 8-126611, and no consideration is given to the easiness of alignment in forward/backward and leftward/rightward motions.

The operation error prevention mechanism presented in the apparatus disclosed in Japanese Patent Laid-Open No. 2003-230535 is effective in an apparatus in which the movable range of an operation target coincides with the operation range of the joystick. For this reason, it is difficult to apply such a mechanism to an apparatus like an ophthalmic apparatus which requires fine motion operation and coarse motion operation and in which the moving range of the inspection unit is sufficiently larger than the moving range of the joystick. In addition, no consideration is given to a sliding mechanism.

In consideration of the above problems, the present invention provides a technique of implementing an electric joystick with a simple arrangement which has operability similar to the sliding operation of a manual joystick.

SUMMARY OF THE INVENTION

According to one aspect of the present invention, there is provided an ophthalmic apparatus in which a tilt angle of an operating rod corresponds to a position of an inspection unit adapted to inspect an eye to be examined, and a movable range of the inspection unit is wider than a tilt able range of the operating rod, the apparatus comprising: a detection unit adapted to detect the tilt angle of the operating rod by detecting an electrical signal generated by tilting the operating rod; a calculation unit adapted to calculate a position of the inspection unit which corresponds to the tilt angle; a moving unit adapted to move the inspection unit to a position calculated by the calculation unit; and a switching unit adapted to switch between interruption and resumption of calculation processing performed by the calculation unit.

Further features of the present invention will be apparent from the following description of exemplary embodiments with reference to the attached drawings.

BRIEF DESCRIPTION OF THE DRAWINGS

FIG. 3 is a system block diagram of the ophthalmic apparatus;

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
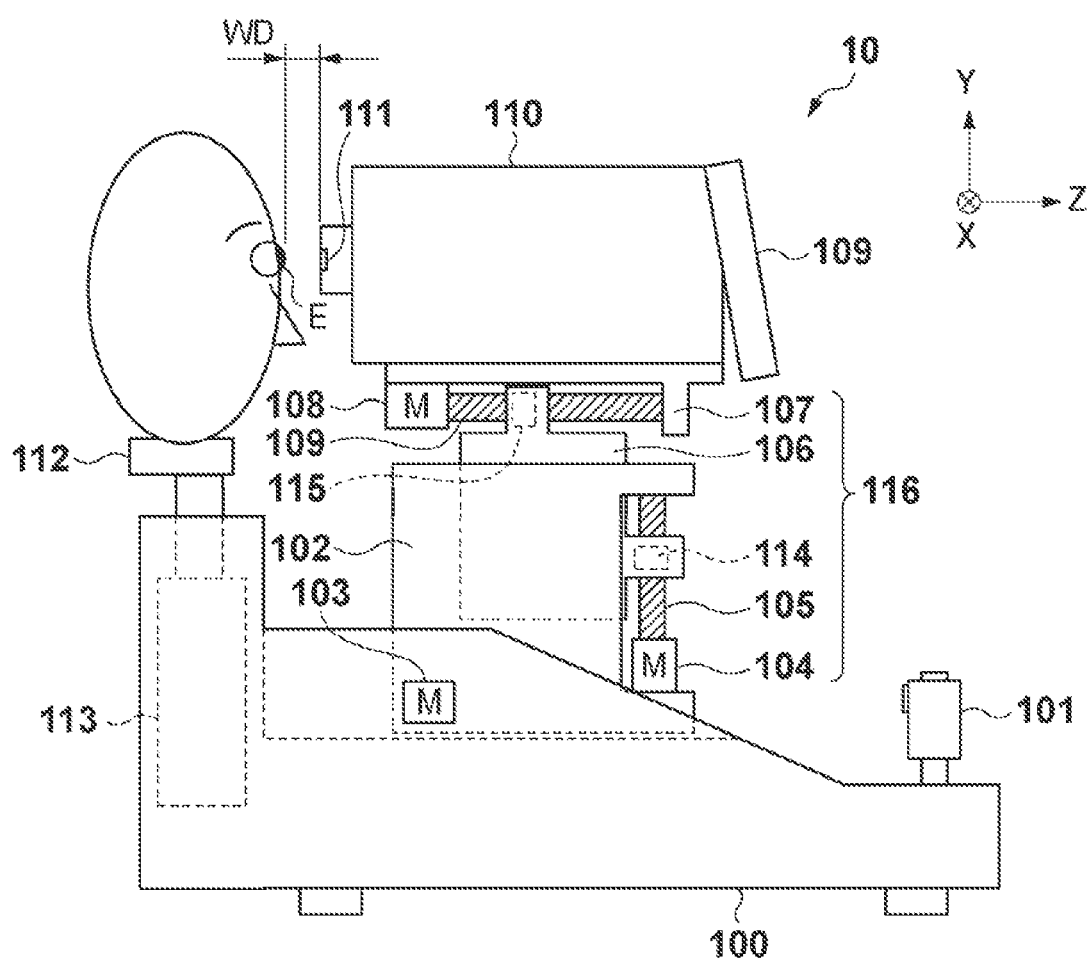
FIG. 1 is a view showing the overall arrangement of an ophthalmic apparatus.

FIG. 1 is a view showing the overall arrangement of an ophthalmic apparatus 10 according to the present invention. The ophthalmic apparatus includes, as main components, a base 100 having a face rest portion 112 which supports the face of an object, a driving unit 116 provided on the base 100, an inspection unit 110 mounted on the driving unit 116, and an electric joystick 101 as an operation member.

Referring to FIG. 1, a frame 102 can move in the left/rightward direction (to be referred to as the X-axis direction hereinafter) relative to the base 100. A driving mechanism in the X-axis direction includes an X-axis driving motor 103 fixed on the base 100, a lead screw (not shown) coupled to the output shaft of the motor, and a nut (not shown) which is fixed to the frame 102 and is movable on the lead screw in the X-axis direction. A rotation signal from a system control unit 201 (to be described later with reference to FIG. 3) is transmitted to the X-axis driving motor 103. The X-axis driving motor 103 then rotates the lead screw to move the frame 102 in the X-axis direction through the nut.

Likewise, a frame 106 can move in the upward/downward direction (to be referred to as the Y-axis direction hereinafter) relative to the frame 102. A driving mechanism in the Y-axis direction includes a Y-axis driving motor 104 fixed on the base 102, a lead screw 105 coupled to the output shaft of the motor, and a nut 114 which is fixed to the frame 106 and is movable on the lead screw in the Y-axis direction. A rotation signal from the system control unit 201 is transmitted to the Y-axis driving motor 104. The Y-axis driving motor 104 then rotates the lead screw to move the frame 106 in the Y-axis direction through the nut.

In addition, a frame 107 can move in the forward/backward direction (to be referred to as the Z-axis direction hereinafter) relative to the frame 106. A driving mechanism in the Z-axis direction includes a Z-axis driving motor 108 fixed on the base 107, a lead screw 109 coupled to the output shaft of the motor, and a nut 115 which is fixed to the frame 106 and is movable on the lead screw in the Z-axis direction. A rotation signal from the system control unit 201 is transmitted to the Z-axis driving motor 108. The Z-axis driving motor 108 then rotates the lead screw to move the frame 107 in the Z-axis direction through the nut.

An inspection unit 110 can be driven separately along the X-, Y-, and Z-axes based on the above drive principles along the respective axes. The system control unit 201 determines the operation amounts of the motors of the respective axes (the X-axis driving motor 103, the Y-axis driving motor 104, and the Z-axis driving motor 108) based on input signals (to be described later) from the joystick 101.

The inspection unit 110 for measurement is fixed on the frame 107. For example, a non-contact type tonometer includes, on the end portion of the inspection unit 110 which is located on the object side, an objective lens 111 for the observation of the anterior eye part and a nozzle (not shown) which is located at the objective lens center and discharges air necessary for eye pressure measurement. An anterior eye part image of the eye E, which has entered from the objective lens 111 for the observation of the anterior eye part, is formed on a CCD 205 (to be described later with reference to FIG. 3) through an optical system (not shown) arranged in the inspection unit 110. An LCD monitor 109 as a display member for the observation of the eye E is provided on the end portion of the inspection unit 110 which is located on the examiner side. The system control unit 201 displays, on the LCD monitor 109, the anterior eye part image formed on the CCD 205 together with alignment indices.

Note that this embodiment is configured to drive the inspection unit 110 in the Y-axis direction based on an electrical signal obtained from the joystick 101. The present invention has a feature that the inspection unit 110 is electrically driven in a two-dimensional plane in the leftward/rightward and forward/backward directions. However, driving operation in the upward/downward direction is not limited to the electric driving scheme. Therefore, the present invention is effective for an ophthalmic apparatus configured to perform driving operation in the upward/downward direction using a mechanical driving scheme typified by a belt transmission mechanism.

Figure 2:
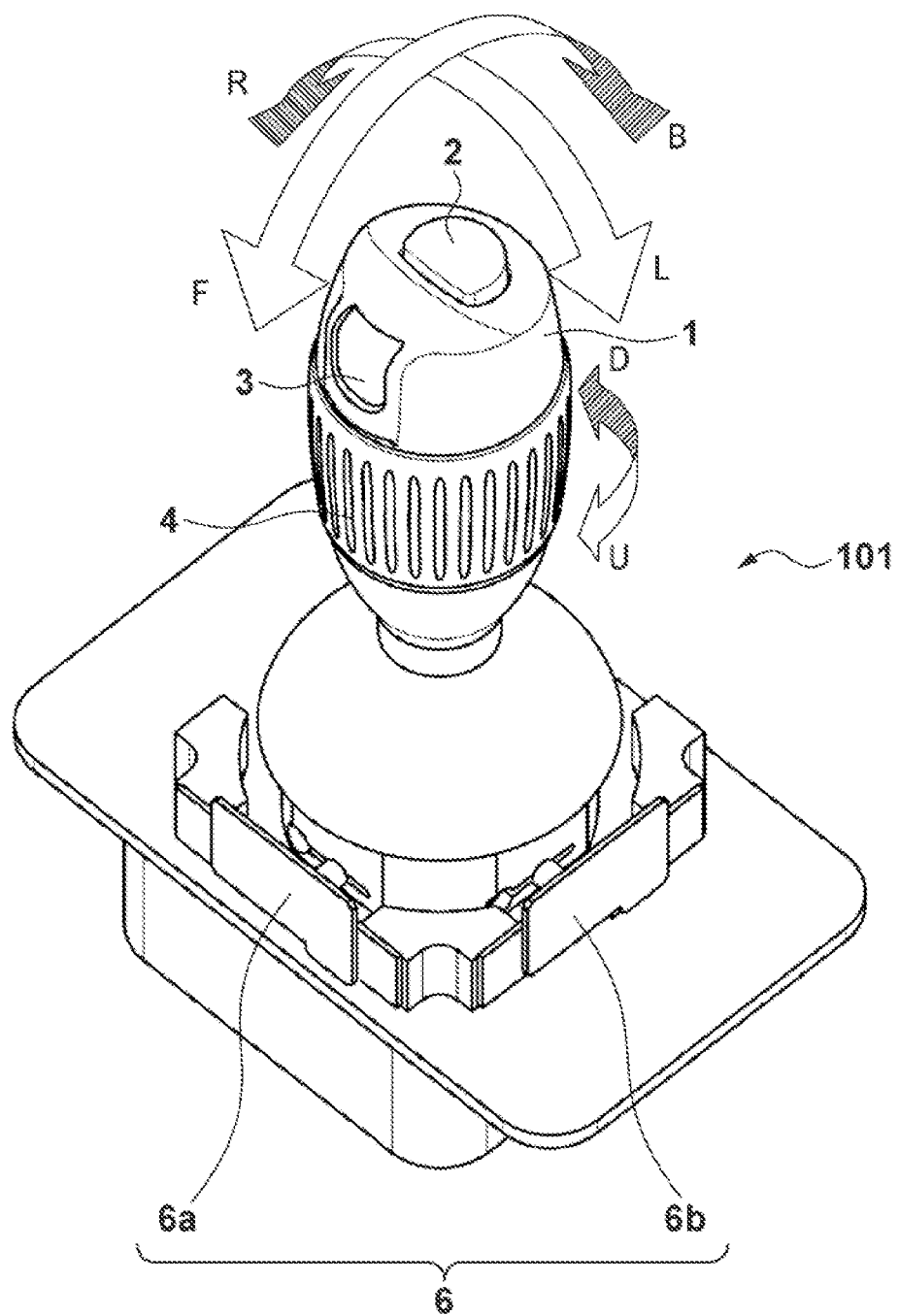
FIG. 2 is a perspective view showing the arrangement of a joystick.

FIG. 2 shows the arrangement of the joystick 101. The joystick 101 includes an operating rod 1, a measurement start switch 2, a measurement unit coordinate holding switch 3, a rotating dial 4, an encoder mechanism 5 (Y-axis encoder input unit 5), and a potentiosensor 6 (X-/Z-axis tilt angle input unit 6).

The operating rod 1 can tilt on a fixed point below the rod as an operation supporting point up to a predetermined angle. The potentiosensor 6 mounted in the joystick detects the tilt of the operating rod 1. The potentiosensor 6 includes two variable resistors 6a and 6b respectively corresponding to the X- and Y-axes, and are positioned to be perpendicular to each other. When the operating rod 1 tilts, the tilting direction is decomposed into X-axis and Z-axis components. It is possible to obtain resistances corresponding to the tilts of the respective axes from the tilt angle. The system control unit 201 (to be described later with reference to FIG. 3) reads the resistances obtained by the potentiosensor 6. This makes it possible to uniquely determine the tilting direction and angle of the operating rod 1. Although this embodiment is described assuming that the potentiosensor 6 is a variable resistor, it is possible to perform detection by using an optical sensor such as a rotary encoder or a magnetic sensor.

The rotating dial 4 is disposed coaxially with the operating rod 1. The rotating dial 4 incorporates an encoder mechanism (not shown) which generates an electrical signal for driving the inspection unit 110 in the Y-axis direction. When the rotating dial 4 rotates counterclockwise about the same axis as that of the operating rod 1, the encoder mechanism detects a rotational angle and rotating direction per unit time. The system control unit 201 determines the moving amount and direction of the inspection unit 110 in the Y-axis direction from detected values, and drives the inspection unit 110 along the Y-axis. The measurement start switch 2 for starting measurement unique to the apparatus is arranged on the upper portion of the operating rod 1. The operating rod 1 further includes the measurement unit coordinate holding switch 3 as an operation change input unit. The measurement unit coordinate holding switch 3 will be described in detail later.

FIG. 3 is a system block diagram of the ophthalmic apparatus 10. The ophthalmic apparatus 10 includes the joystick 101, the system control unit 201, the X-/Z-axis tilt angle input unit 6, the Y-axis encoder input unit 5, the measurement start switch 2, the measurement unit coordinate holding switch 3, various types of sensor input units 202, an operation panel 203, a memory 204, the CCD 205, the LCD monitor 109, a measurement light source 207, a chin rest motor 113, the X-axis driving motor 103, the Y-axis driving motor 104, and the Z-axis driving motor 108. The system control unit 201 controls various types of constituent elements to detect various kinds of input signals, analyze the input signals, and control various kinds of output operations. In this case, the joystick 101, the LCD monitor 109, the chin rest motor 113, the X-axis driving motor 103, the Y-axis driving motor 104, and the Z-axis driving motor 108 correspond to the respective reference numerals in FIG. 1. The measurement start switch 2, the measurement unit coordinate holding switch 3, the Y-axis encoder input unit 5, and the X-/Z-axis tilt angle input unit 6 correspond to the respective reference numerals in FIG. 2.

The sensor input units 202 is a limit sensor or the like which detects the movement limit of the driving unit. The operation panel 203 is a panel for allowing the examiner to make various kinds of settings. The memory 204 is a memory capable of writing and reading various kinds of data. The CCD 205 captures an image of the eye E. The measurement light source 207 illuminates the eye E with light.

A method of controlling the inspection unit 110 when the examiner operates the joystick 101 will be described in detail. When the examiner tilts the operating rod 1 in an arbitrary direction, the potentiosensor 6 decomposes the tilt into X-axis and Y-axis components. The respective axis components of the tilt angle are detected as resistances, which are then transmitted to the system control unit 201 via an A/D converter (not shown).

Figure 4:
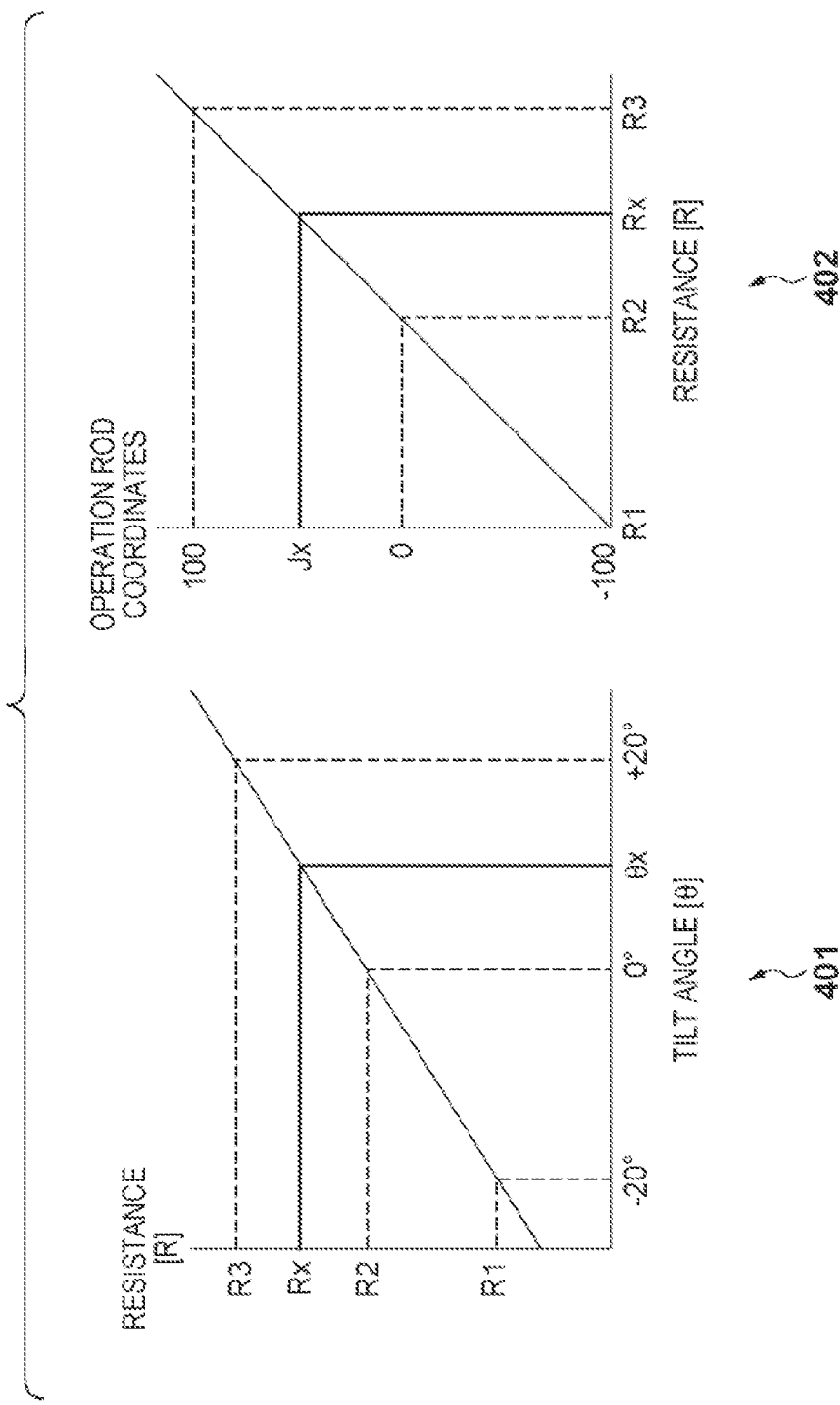
FIG. 4 is a view for explaining coordinate position transformation.

FIG. 4 is a view for explaining a method of calculating position coordinates from the tilt angle of the operating rod 1 by the system control unit 201. The system control unit 201 performs transformation by the same method with respect to the X- and Y-axes. For the sake of easy understanding, the following description will be made with reference to only the X-axis.

Reference numeral 401 denotes the relationship between the tilt angle of the X-axis and the resistance. When the operating rod 1 is at the upright position, the tilt angle is 0°, and hence the resistance is $R2[\Omega]$. The operating rod 1 can tilt up to ±20°. When the operating rod 1 tilts to the maximum tilt angles, the corresponding resistances are $R1[\Omega]$ and $R3[\Omega]$, respectively, according to the relationship 401. This embodiment uses a mechanism which provides a mechanical stopper for protection for the operating rod 1 so as not to use the entire region of the potentiosensor 6 in order to prevent a load from being imposed on the potentiosensor 6 when the operating rod 1 tilts to the maximum angle.

Reference numeral 402 denotes the relationship between resistance and operating rod coordinates. The system control unit 201 calculates the position coordinates of the operating rod 1 from read resistances by using the relationship 402. When the resistance is R2, the position coordinate is "0". When the resistances are R1 and R3, the position coordinates are transformed into "−100" and "100", respectively.

Assume that the examiner has tilted the operating rod 1 through a tilt angle θx in the X-axis direction (rightward direction). At this time, the system control unit 201 reads the resistance represented by Rx, and transforms it into a position coordinate J(x). The system control unit 201 performs transformation with respect to the Z-axis in the same manner as described above. When the examiner tilts the operating rod 1 through θz in the Z-axis direction, the Z-axis coordinate position of the operating rod 1 is J(z).

When the examiner tilts the operating rod 1 in an oblique direction, the tilt angle is decomposed into X-axis and Z-axis components, which are then calculated as position information J(x, z) by using the above transformation.

The maximum coordinate range of the operating rod 1 and the maximum movable range of the inspection unit 110 will be described with reference to FIG. 5. Reference numeral 501 denotes the maximum coordinate range of the operating rod 1 which is transformed from the tilt angle of the operating rod 1; and 502, the maximum movable range of the inspection unit 110 represented by coordinates.

Figure 5:
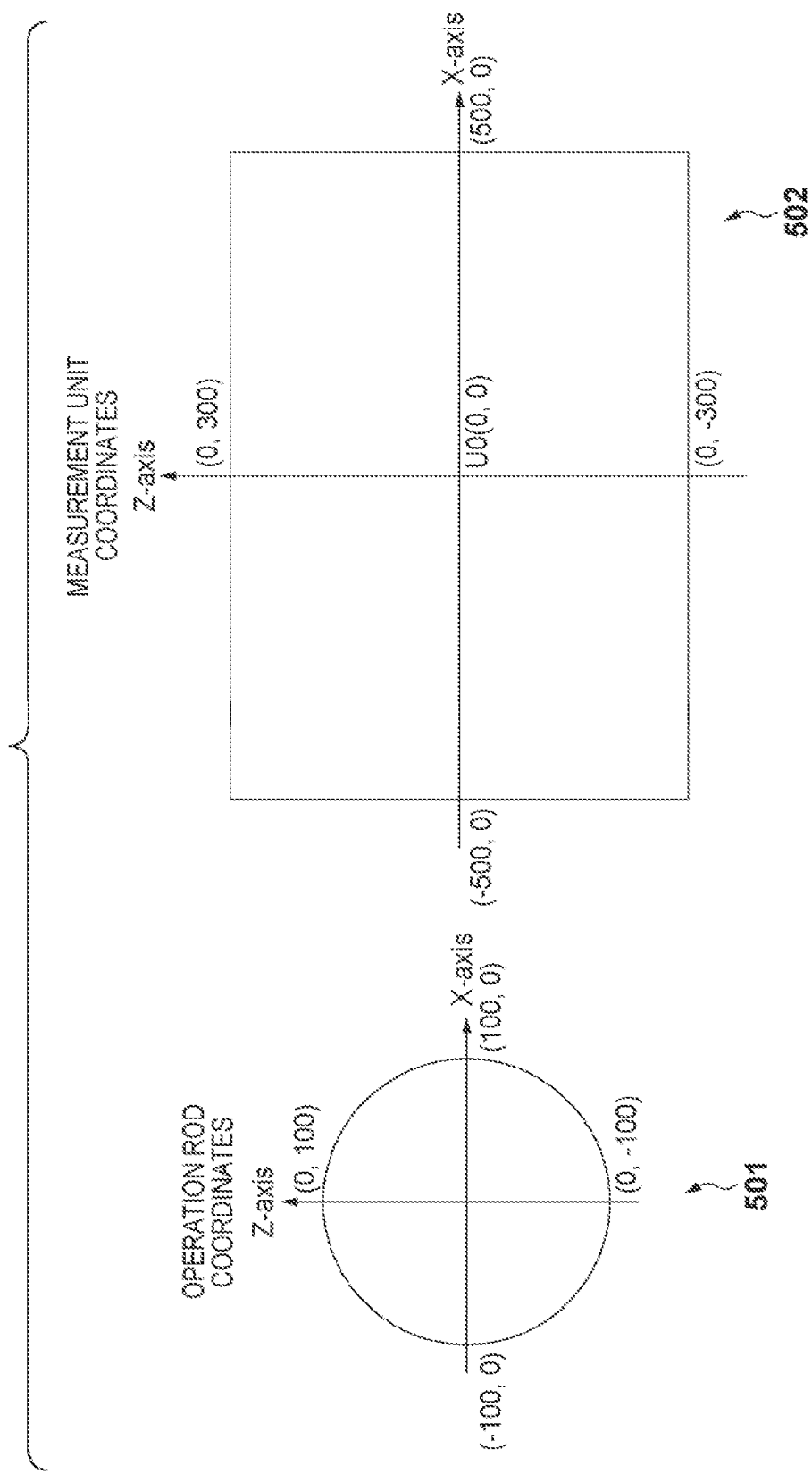
FIG. 5 is a view showing the coordinate ranges of an operating rod and inspection unit.

Consider only the X-axis direction in FIG. 5. In this case, obviously, the movable range (from −500 to 500) of the inspection unit 110 is sufficiently larger than the tilt range (from −100 to 100) of the operating rod 1. This is one of the major features of a general ophthalmic apparatus. This indicates that the tilt angle of the operating rod corresponds to the position of the inspection unit which inspects the eye to be examined, and the movable range of the inspection unit is larger than the tiltable range of the operating rod.

The inspection unit 110 of the ophthalmic apparatus needs to measure both the left and right eyes to be examined, and hence requires a movable range corresponding to the width of the left and right eyes, in addition to a movable range required for detailed alignment of each eye to be examined. On the other hand, it is required for the joystick 101 to have a fine alignment function for each eye to be examined. If the movable range of the inspection unit 110 coincides with the movable range of the operating rod 1, the moving amount of the inspection unit 110 becomes too large relative to the tilt angle of the operating rod 1. This makes it impossible to perform fine alignment.

Figure 6:
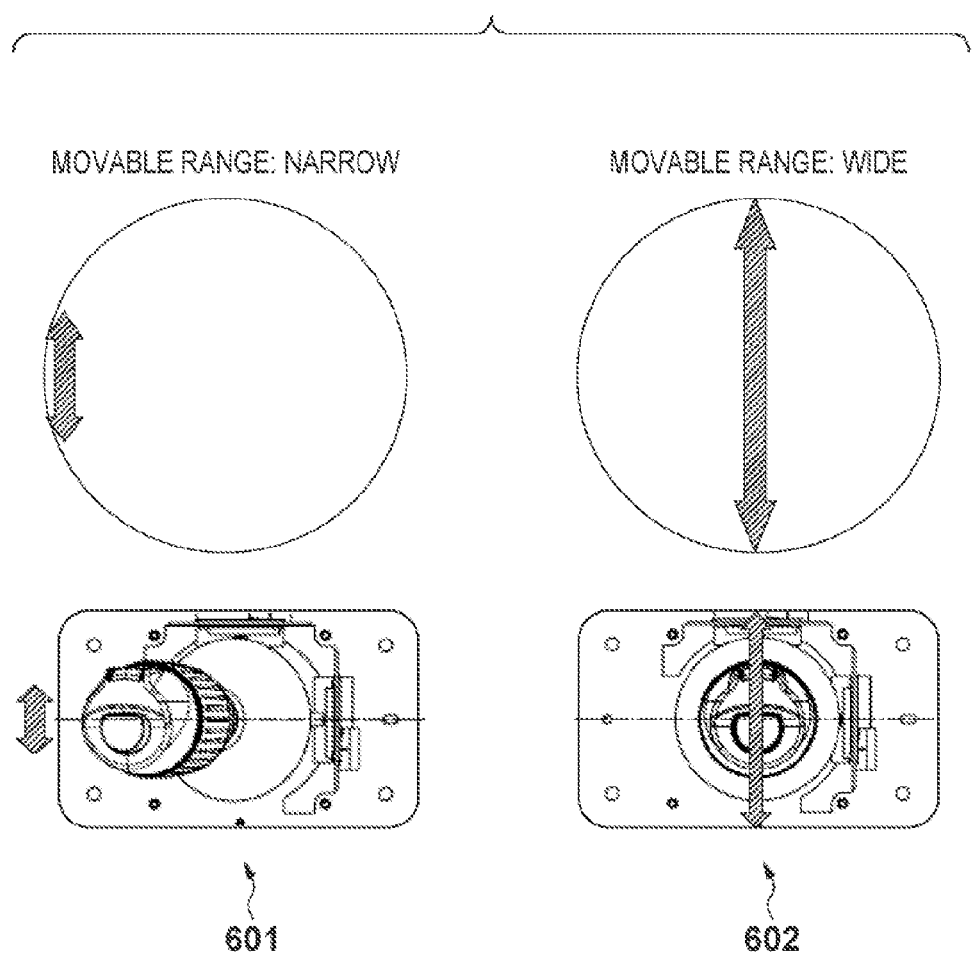
FIG. 6 is a view showing the Z-axis direction movable range of the operating rod.

FIG. 6 shows movable ranges in the Z-axis direction in a state 601 in which the operating rod 1 tilts to the left and a state 602 in which the operating rod 1 is at the central position (that is, a tilt angle of (0°), respectively. The joystick 101 has a circular movable range for securing its maximum operation region. For this reason, in this structure, when the operating rod 1 is at the central position, the movable range in the Z-axis direction is maximum, whereas as the tilt angle in the X-axis direction increases, the movable range in the Z-axis direction decreases. Obviously, in this structure, when the operating rod 1 tilts in the Z-axis direction, the movable range in the X-axis direction decreases. In addition, when the examiner tries to largely move the operating rod 1 in the Z-axis direction while the tilt angle in the X-axis direction is large, the operating rod 1 tilts toward the center of the X-axis along an edge of its movable range. That is, the tilt angle of the X-axis cannot be maintained.

Control at the time of alignment according to this embodiment will be described next with reference to the flowchart of FIG. 7 and FIGS. 8 to 10.

Figure 7:
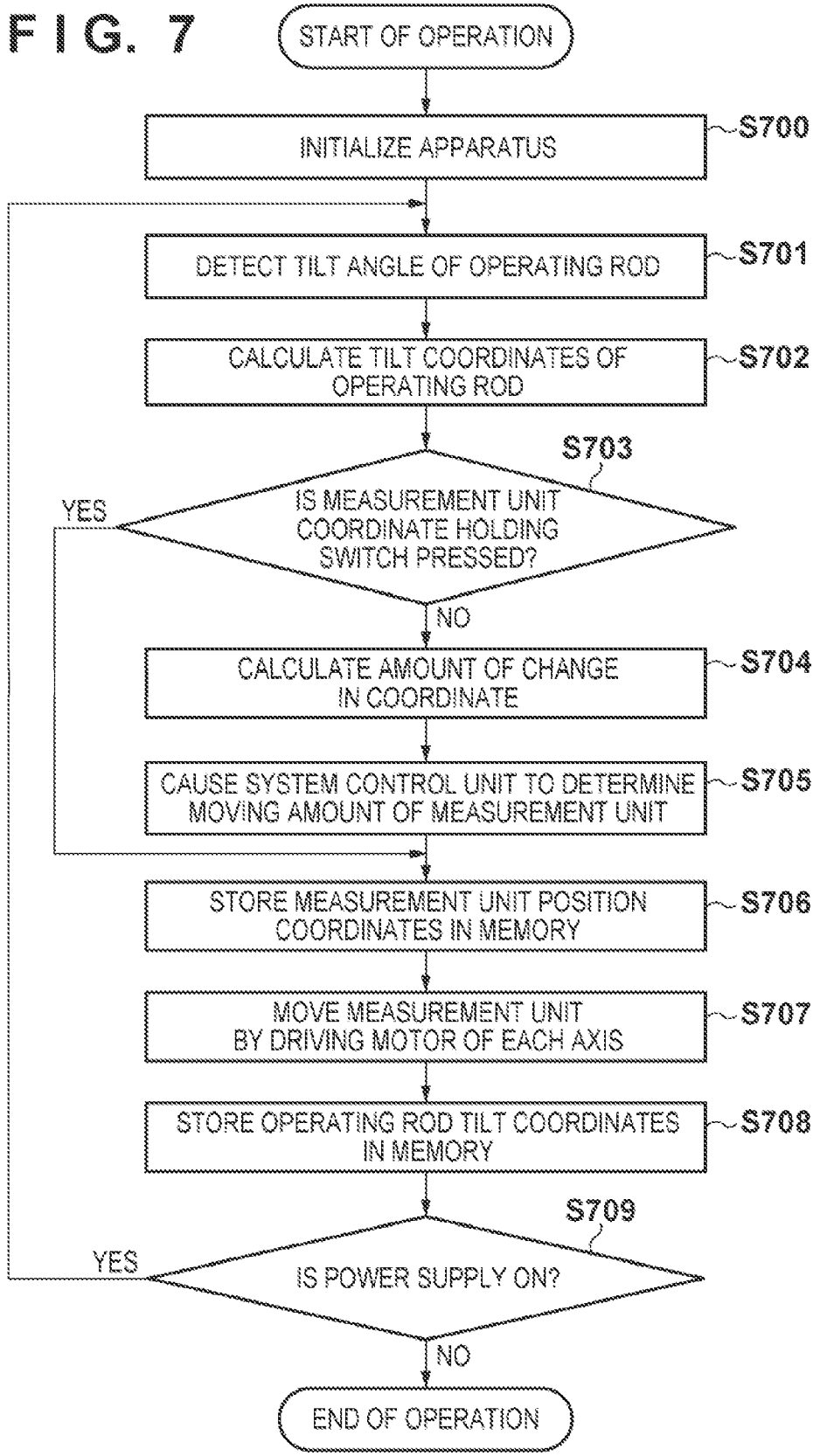
FIG. 7 is a flowchart showing a processing procedure in an ophthalmic apparatus.

In step S700 in FIG. 7, the system control unit 201 initializes the ophthalmic apparatus. In this initialization processing, the system control unit 201 moves the inspection unit 110 to the initial position as the coordinate origin by driving the respective three-axis motors. In addition, the system control unit 201 makes origin coordinates J(0, 0) of the upright position of the operating rod 1 of the driving unit coincide with origin coordinates U(0, 0) of the inspection unit 110. Subsequently, the system control unit 201 performs control to repeat each of the processes in steps S701 to S708 (to be described below) until the ophthalmic apparatus is powered off.

In step S701, when the examiner tilts the operating rod 1 upon starting measurement of the eye to be examined, the system control unit 201 starts detecting the tilt angle of the operating rod 1 based on an electrical signal.

In step S702, the system control unit 201 starts the processing of transforming the detected tilt angle into the position coordinates of the operating rod 1 by the resistance-coordinate transformation described with reference to FIG. 4.

In step S703, the system control unit 201 determines whether an input signal is detected after the measurement unit coordinate holding switch 3 is pressed. Upon determining that the measurement unit coordinate holding switch 3 has been pressed (YES in step S703), the process advances to step S706. Upon determining that the measurement unit coordinate holding switch 3 has not been pressed (NO in step S703), the process advances to step S704.

In step S704, the system control unit 201 calculates difference information $\Delta J$ between position coordinates $J_{n-1}$ of the operating rod 1, stored in the memory 204, and current position coordinates $J_n$. If, for example, the position coordinates stored in the memory 204 are $J_{n-1}$(50, 50), and the current position coordinates are $J_n$(60, 40), the difference information of the operating rod coordinates is calculated as $\Delta J$(10, −10).

In step S705, the system control unit 201 determines a moving amount $\Delta U$ of the inspection unit 110 based on the difference information $\Delta J$ of the operating rod coordinates. In the ophthalmic apparatus of this embodiment, the operation of the joystick 101 one-to-one corresponds to the moving amount of the inspection unit 110. If, therefore, the difference information is $\Delta J$(10, −10), the system control unit 201 determines the moving amount of the inspection unit 110 as $\Delta U = \Delta J$(10, −10) in the same manner as described above.

In step S706, the system control unit 201 determines the position coordinates of the inspection unit 110 after movement based on the moving amount AU of the inspection unit 110. The system control unit 201 obtains the position coordinates of the inspection unit 110 after movement according to $U_n = U_{n-1} + \Delta U$, and stores the calculation result in the memory 204. At this time, if the position coordinates after movement exceed the movable range of the inspection unit 110 denoted by reference numeral 502 in FIG. 5, the extreme value of the movable range is stored as a calculation result in the memory 204. Upon determining in step S703 that the examiner has pressed the measurement unit coordinate holding switch 3, the system control unit 201 does not perform any of the processes in steps S704 and S705, and hence determines the difference information of the operating rod position as $\Delta J$="0" and does not update the position coordinates U of the inspection unit 110.

In step S707, the system control unit 201 moves the position of the inspection unit 110 by transmitting driving signals to the X-axis driving motor 103 and the Z-axis driving motor 108 based on the determined position coordinates U of the inspection unit 110.

That is, depending on whether the measurement unit coordinate holding switch 3 is pressed, the system control unit 201 executes switching between interruption of calculation processing of calculating the position of the inspection unit 110 after movement and resumption of the calculation processing.

In step S708, the system control unit 201 stores the information of the coordinate position of the operating rod 1 as $J_{n-1}$ in the memory 204.

In step S709, the system control unit 201 determines whether the power supply of the ophthalmic apparatus is ON. If the power supply is ON (YES in step S709), the process returns to step S701. If the power supply is OFF (NO in step S709), the system control unit 201 terminates the processing.

Figure 8:
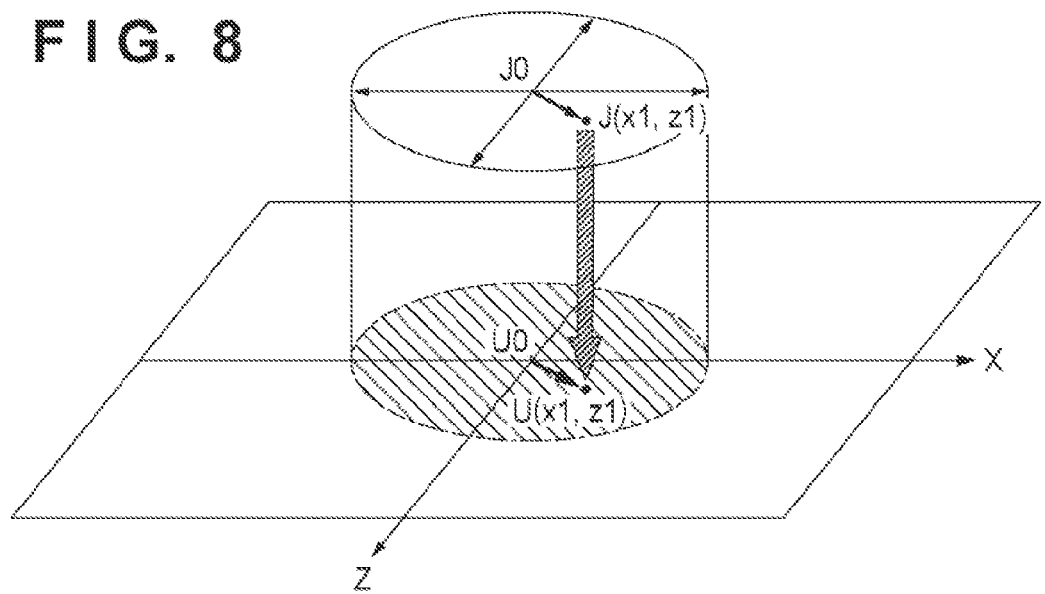
FIG. 8 is a view showing the correspondence relationship between the coordinates of the operating rod and inspection unit.

FIG. 8 shows the relationship between the position coordinates of the operating rod 1 immediately after the power supply is turned on and the position coordinates of the inspection unit 110, and the position coordinates of the operating rod 1 and inspection unit 110 when the measurement unit coordinate holding switch 3 is not pressed. The region indicated by the hatched portion in FIG. 8 is the projection of the tilt region of the operating rod 1 onto the operation region of the inspection unit 110. This range has a circular shape having the same radius as that of the coordinate range of the operating rod 1, that is, "100", with $U_0$ being the origin.

When the system control unit 201 performs initialization immediately after the power supply is turned on, the origin coordinates J(0, 0) of the upright position of the operating rod 1 of the driving unit coincide with the origin coordinates U(0, 0) of the inspection unit 110.

The respective position coordinates stored in the memory 204 are $J_{n-1} = J_0 = (0, 0)$, and $U_{n-1} = U_0 = (0, 0)$. When the examiner tilts the operating rod 1 to move it from the origin $J_0$ to J(x1, z1), the system control unit 201 calculates difference information ΔJ(x1, z1). Upon obtaining the difference information ΔJ, the system control unit 201 calculates the moving amount ΔU, and determines position coordinates $U_n$ of the destination according to $U_n = U_{n-1} + \Delta U$, thereby obtaining $U_n = (0, 0) + (x1, z1) = (x1, z1)$.

The system control unit 201 moves the inspection unit 110 to $U_n$ by driving each motor based on obtained coordinate information. Upon completing the movement, the system control unit 201 stores the position information $J_n$ of the operating rod 1 and the position information $U_n$ of the inspection unit 110 as $J_{n-1}$ and $U_{n-1}$ in the memory 204.

When the examiner operates the joystick 101 without pressing the measurement unit coordinate holding switch 3, the system control unit 201 drives the inspection unit 110 by repeating the above series of control operations. When, therefore, the examiner tilts the operating rod 1 in the leftward/rightward direction (X-axis direction), the inspection unit 110 moves in the eye-width direction (X-axis direction) of the eye to be examined by an amount corresponding to the tilt angle. Likewise, when the examiner tilts the operating rod 1 in the forward/backward direction (Z-axis direction), the inspection unit 110 moves in a direction to approach or separate from the eye to be examined (Z-axis direction).

That is, the examiner can freely drive the inspection unit 110 within the region indicated by the hatching by tilting the operating rod 1.

Control to be performed when the measurement unit coordinate holding switch 3 is pressed will be described next with reference to FIG. 9. The following description is based on the assumption that the tilting operation described with reference to FIG. 8 has moved the position coordinates of the inspection unit 110 to a position U(x1, z1).

Obviously, when the position coordinates of the inspection unit 110 are U(x1, z1), the position coordinates of the operating rod 1 are J(x1, z1). When the examiner presses the measurement unit coordinate holding switch 3, the system control unit 201 does not update the coordinate position U(x1, z1) stored in the memory 204. For this reason, even if the examiner returns the operating rod 1 from the position coordinates J(x1, z1) to a neutral state $J_0$ while pressing the measurement unit coordinate holding switch 3, the inspection unit 110 is not driven. When the examiner releases the measurement unit coordinate holding switch 3 while the position coordinates of the operating rod 1 are in the state of $J_0$, the system control unit 201 starts updating the position coordinates of the inspection unit 110 again, and each of the processes in steps S701 to S708 allows the examiner to perform the inspection unit 110.

Figure 9:
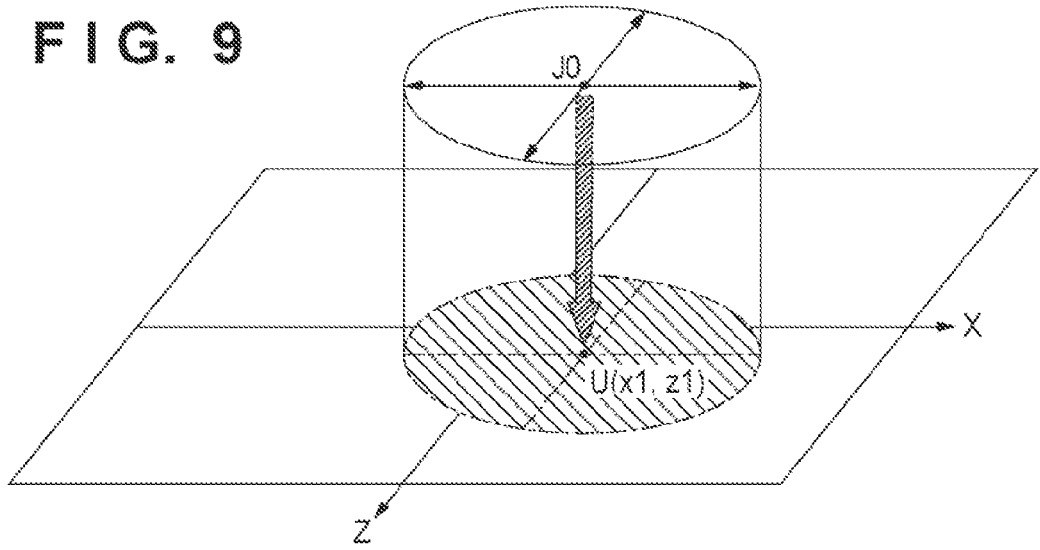
FIG. 9 is a view showing the correspondence relationship between the coordinates of the operating rod and inspection unit.

In this case, the hatched portion in FIG. 9 indicates the movable range of the inspection unit 110 after the above control. The movable range of the inspection unit 110 set when the examiner operates the joystick 101 coincides with the circular region with a radius of "100" centered on the origin position $U_0$ in FIG. 8. In contrast to this, after this control operation, the origin position U(x1, z1) has greatly changed, although the movable range is a circular region with the same radius.

Figure 10:
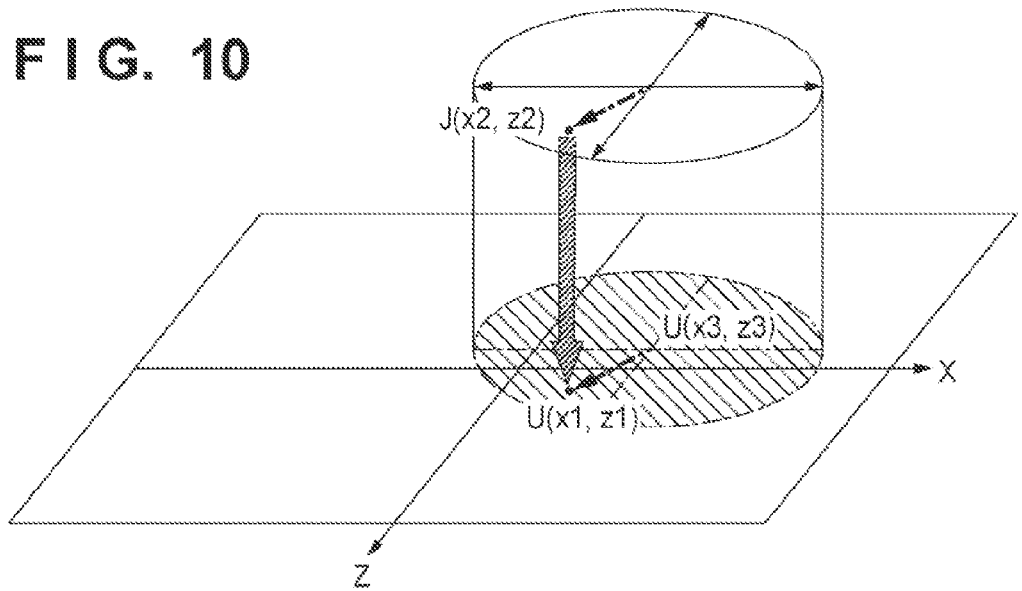
FIG. 10 is a view showing the correspondence relationship between the coordinates of the operating rod and inspection unit.

The movable range of the inspection unit 110 will be described next with reference to FIG. 10, which is set when the examiner releases the measurement unit coordinate holding switch 3 while the position coordinates of the operating rod 1 are J(x2, z2). The following description will be continued on the assumption that the position coordinates of the inspection unit 110 set when the examiner presses the measurement unit coordinate holding switch 3 coincide with the position coordinates U(x1, z1) at the end of the operation in FIG. 8 as in the explanation with reference to FIG. 9.

Although mentioned above, while the examiner presses the measurement unit coordinate holding switch 3, the system control unit 201 holds the position coordinates U(x1, z1) of the inspection unit 110. For this reason, even when the examiner moves the operating rod 1 from J(x1, z1) to J(x2, z2), the system control unit 201 does not drive the inspection unit 110. However, when the examiner releases the measurement unit coordinate holding switch 3 after moving the operating rod 1 to the position indicated by J(x2, z2), the system control unit 201 starts to associate the position coordinates of the inspection unit 110 with the position coordinates of the operating rod 1. With this control, the movable range of the inspection unit 110 becomes a circular region having the same radius with the tilt supporting point being the origin. In this case, position coordinates U(x3, z3) of the origin center are calculated by $U(x3, z3) = (x1, z1) - (x2, z2) = ((x1-x2), (z1-z2))$.

As described above, operating the measurement unit coordinate holding switch 3 makes it possible to validate or invalidate the operation of the inspection unit 110 with respect to the operating rod 1, and to change the movable region.

This control has the same function as that of the sliding operation when the mechanical joystick is operated. This allows the electric joystick to reproduce sliding operation similar to that of a manual joystick by performing control according to this embodiment.

Finally, an actual measurement procedure using control according to this embodiment will be described. Immediately after the ophthalmic apparatus is powered on, the system control unit 201 initializes the inspection unit 110. In addition, the system control unit 201 reads out correction information about the apparatus stored in the memory 204 to perform gain setting for the CCD 205, initialization for the measurement light source 207, and the like.

First of all, when starting measurement, the examiner lets an object as a measurement target rest his/her chin on the face rest portion 112 and his/her forehead on a forehead rest portion (not shown), thereby fixing the eye to be examined. The examiner can adjust the face rest portion 112 in accordance with the size of the face of the object in the Y-axis direction (upward/downward direction) by using the chin rest motor 113. The examiner adjusts the chin rest at an optimal height in accordance with the size of the face of the object by operating a chin rest up/down switch (not shown) disposed on the operation panel 203.

Figure 11:
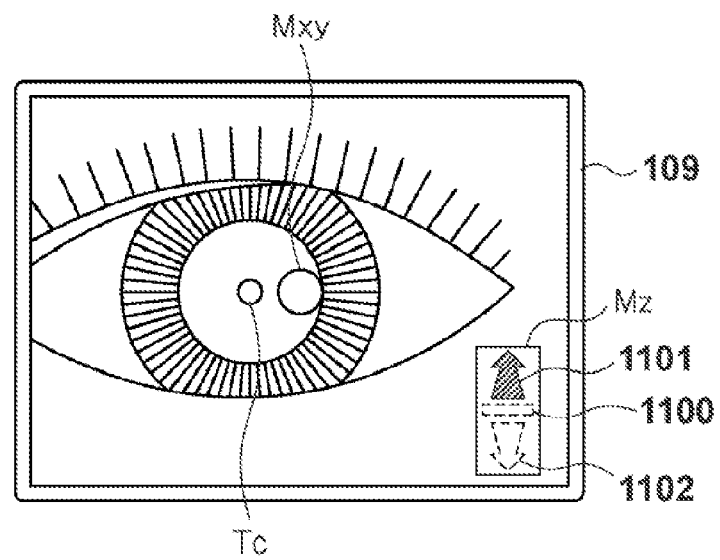
FIG. 11 is a view for explaining anterior eye part alignment indices.

The examiner then aligns the inspection unit 110 with the eye E by operating the joystick 101 while observing the eye E displayed on the LCD monitor 109. FIG. 11 is a view for explaining an anterior eye part image of the eye E and alignment indices on the LCD monitor 109. Reference symbol Tc denotes the pupil center of the eye E; and Mxy and Mz, alignment indices synthesized by the system control unit 201.

When aligning the inspection unit 110 in the upward/downward and leftward/rightward directions, the examiner operates the joystick 101 so as to make the pupil center Tc of the eye E enter the alignment mark Mxy while observing the LCD monitor 109. The ophthalmic apparatus is structured such that when the eye E coincides with the optical axis of the inspection unit 110, the pupil center Tc enters the alignment index Mxy.

Although a detailed description of the ophthalmic apparatus according to this embodiment will be omitted, a description of the apparatus will be continued on the assumption that it can automatically detect the Z-axis direction distance WD between the eye E and the inspection unit 110. The system control unit 201 detects the distance WD between the eye E and the inspection unit 110, and notifies the examiner of the positional relationship between the eye E and the inspection unit 110 by using the alignment index Mz. If the distance WD is optimal for measurement, an icon 1100 in the alignment index Mz is displayed. If the distance WD is longer than the distance to the optimal position, it is necessary to move the inspection unit 110 in a direction to approach the eye E, that is, in the positive Z-axis direction. Therefore, an upward arrow icon 1101 is displayed. In contrast, if the distance WD is shorter than the distance to the optimal position, that is, the inspection unit 110 is close to the eye E, it is necessary to move the inspection unit 110 in a direction to separate, that is, the negative Z-axis direction. Therefore, a downward arrow icon 1102 is displayed. Upon aligning the inspection unit 110 to the optimal alignment position while watching the anterior eye part image of the eye E and icons of the two alignment indices Mxy and Mz displayed on the LCD monitor 109, the examiner presses the measurement start switch 2 to start measurement.

If the eye E and the alignment indices displayed on the LCD monitor 109 have the relationship shown in FIG. 11 upon completion of fixing of the eye to be examined, it is necessary to perform alignment. By watching the LCD monitor 109, the examiner can know that it is necessary to move the inspection unit 110 in the leftward direction relative to the eye E and in a direction to approach the eye E to perform alignment.

First of all, in order to move the inspection unit 110 in the leftward direction, the examiner tilts the operating rod 1 in the leftward direction while releasing the measurement unit coordinate holding switch 3. When the examiner tilts the operating rod 1 in the leftward direction, the inspection unit 110 moves in the leftward direction in accordance with the tilt angle of the rod. The examiner increases the tilt angle of the operating rod 1 until the alignment index Mxy coincides with the eye center Tc of the object while observing them. When the alignment index Mxy coincides with the pupil center Tc, the examiner stops tilting the operating rod 1, thus finishing the alignment in the X-axis direction.

Since the alignment in the X-axis direction is complete, the examiner starts alignment in the Z-axis direction. Note, however, that since the operating rod 1 has tilted in the leftward direction, it is difficult to perform alignment in the Z-axis direction in this state. For this reason, the examiner returns the operating rod 1 to the neutral position while pressing the measurement unit coordinate holding switch 3. At this time, since the system control unit 201 stops driving the inspection unit 110, the examiner can operate the operating rod 1 without moving the X-axis position of the inspection unit 110.

After the operating rod 1 returns to the neutral state, the examiner operates the inspection unit 110 in accordance with an instruction represented by the alignment index Mz, thereby finishing the alignment.

In this embodiment, the examiner performs alignment in the X-axis direction first, and then performs alignment in the Z-axis direction. However, the examiner may perform alignment in the reverse order.

The above control allows the examiner to perform operation similar to that of a conventional manual joystick mechanism, thereby providing an electric joystick mechanism which gives no sense of discomfort to the examiner.

According to the present invention, it is possible to implement an electric joystick with a simple arrangement which has operability similar to that of the sliding operation of a manual joystick.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-042658 filed on Feb. 28, 2011, which is hereby incorporated by reference herein in its entirety.

What is claimed is:

1. An ophthalmic apparatus in which a tilt angle of an operating rod corresponds to a position of an inspection unit adapted to inspect an eye to be examined, the apparatus comprising:
    a detection unit adapted to detect the tilt angle of the operating rod by detecting an electrical signal generated by tilting the operating rod;
    a calculation unit adapted to calculate positional coordinates of the operating rod which correspond to respective tilt angles and to calculate a position of the inspection unit from changes in the calculated positional coordinates;
    a moving unit adapted to move the inspection unit to a position calculated by said calculation unit; and
    a switching unit adapted to switch between interruption and resumption of calculation processing of the position of the inspection unit performed by said calculation unit.

2. The apparatus according to claim 1, wherein when said switching unit interrupts the calculation processing, said moving unit holds a position of said detection unit set when said switching unit has interrupted the calculation processing even if the operating rod tilts.

3. The apparatus according to claim 1, wherein the tiltable range of the operating rod comprises a circumference of a circle centered on a tilt supporting point of the operating rod and an interior portion of the circle.

4. The apparatus according to claim 1, wherein said switching unit switches between interruption and resumption of the calculation processing depending on whether a button arranged on the operating rod is pressed.

* * * * *